United States Patent [19]
McPhee

[11] 3,978,857

[45] Sept. 7, 1976

[54] SYSTEM WITH FILTER FOR ADMINISTRATING PARENTERAL LIQUIDS

[75] Inventor: Charles J. McPhee, Sylmar, Calif.

[73] Assignee: American Hospital Supply Corporation, Evanston, Ill.

[22] Filed: Feb. 3, 1975

[21] Appl. No.: 546,509

Related U.S. Application Data

[62] Division of Ser. No. 280,542, Aug. 14, 1972, Pat. No. 3,882,026.

[52] U.S. Cl.............................. 128/214 R; 210/446
[51] Int. Cl.².......................................... A61M 5/14
[58] Field of Search....... 55/159; 128/214 R, 214 C, 128/214 D, 214.2, 218 R, 221; 210/23, 99, 435, 451, 455, 446, 479, 510, DIG. 23

[56] References Cited
UNITED STATES PATENTS

| | | | |
|---|---|---|---|
| 966,963 | 8/1910 | Steinkoenig | 210/455 |
| 2,222,123 | 11/1940 | Schwab | 210/99 |
| 2,660,167 | 11/1953 | Polacco | 128/214 |
| 2,765,923 | 10/1956 | Novak | 210/164 |
| 2,923,669 | 2/1960 | Poitras | 195/103.5 |
| 3,157,481 | 11/1964 | Bujan | 55/417 |
| 3,295,684 | 1/1967 | Webb | 210/446 |
| 3,386,585 | 6/1968 | Weyand et al. | 210/445 |
| 3,471,019 | 10/1969 | Trasen et al. | 210/94 |
| 3,631,654 | 1/1972 | Riely | 55/159 |
| 3,650,093 | 3/1972 | Rosenburg | 55/159 |
| 3,658,183 | 4/1972 | Best et al. | 210/446 |
| 3,753,500 | 8/1973 | Voegeli | 210/446 |

*Primary Examiner*—Thomas G. Wyse
*Assistant Examiner*—Ivars Cintins
*Attorney, Agent, or Firm*—Larry N. Barger; Robert T. Merrick

[57] ABSTRACT

A device for filtering a parenteral solution immediately before it is infused into a patient's vein. The device has a hollow housing containing a "depth" filter membrane of nonfibrous hydrophobic material having randomly connected stacked passages of from 10 to 40 micron size through the filter. After the filter membrane has had one surface in contact with the parenteral solution for a period of 15 to 60 seconds while passing only a minute amount of liquid it is then manually tapped to send a shock wave through the filter. This shock wave unexpectedly causes the hydrophobic filter to freely pass liquid and filter out more than 90 percent of all particulate matter of 5 micron size and larger from the parenteral solution. The large pore hydrophobic filter membrane can perform these filtering efficiencies with a very small, thin disc-shaped membrane of approximately ¼ inch effective diameter.

8 Claims, 11 Drawing Figures

SYSTEM WITH FILTER FOR ADMINISTRATING PARENTERAL LIQUIDS

This is a division of application Ser. No. 280,542 filed Aug. 14, 1972, now U.S. Pat. No. 3,882,026.

BACKGROUND

Parenteral solutions such as normal saline, 5% dextrose, etc., are commonly infused into a patient's vein to replenish liquid and correct electrolyte imbalances. This is often done with a 1-liter bottle suspended mouth downwardly above the patient and liquid flows by gravity from the bottle and through a flexible administration line connected to the bottle and then through a needle inserted into the patient's vein.

The bottle of parenteral solution being infused into the patient has been sterilized either at the manufacturer of the bottled solution or at the hospital where hospitals make up their own solutions. Likewise the tubular administration set connected to the bottle has also been sterilized. While the solution, bottle and administration set are sterile, the solution might pick up a minute amount of sterile particulate matter in the micron size range. These particles could come from various sources such as the bottle, closure, or inner surface of the administration set.

In the past it has been proposed to place a so-called "final filter" at a lower end of the administration set immediately before it enters the venous needle and the patient's vein. While it would be desirable to filter out all sterile particulate matter regardless of how infinitesimally small, as a practical matter filters that would not pass any particles at all also would not pass liquid. With a working practical filter it is desirable to filter out 90 percent or more of all the sterile particulate matter 5 micron or above in size from a sterile parenteral solution.

The problem with previous filters that filtered out 90 percent of all particulate matter 5 micron or above size was the physical size of the filter. These previous filters were roughly the size of a silver dollar and presented a large and cumbersome unit hanging on a needle stuck in the patient's vein. Most of the prior filters were of the "absolute" type, with a series of holes of a given size passing straight through the filter for conducting liquid through the filter while physically blocking particle passage. A woven screen is an example of an absolute filter. Thus to filter out particles of larger than 5 micron the holes must be 5 micron size or smaller. The problem with the absolute filter was that occasionally one hole would be larger than the others and allow some larger particles through. Therefore, an absolute filter rated for 0.45 micron pore size might only filter out 95 percent of all particles of 5 micron and larger. To get liquid to flow through a 0.45 micron related absolute filter a very large surface area was required. An area of 1 inch diameter was not uncommon. Another reason for the large size of prior filters was that they were of hydrophilic or readily "wettable" materials that had an absorbing effect on the liquid. While liquid would pass through such hydrophilic filters, large surface areas were required to get the liquid flow to a rate normally used in intravenous administration.

SUMMARY OF THE INVENTION

I have overcome the problem of previous "final filters" at the patient's venous needle by providing a filter of substantially smaller size. Instead of an absolute filter of 1 inch diameter I have discovered that very high filtering efficiencies are obtained by passing the parenteral solution through a small filter disc of roughly ¼ inch in diameter. This tiny filter disc fits into a housing that is very convenient and compact for attaching directly to a venous needle.

The filter disc of my invention involves a hydrophobic nonfibrous "depth" filter with interconnecting stacked passages of from 10 to 40 micron size. This is entirely different from "absolute" filters of the past which had only a single layer of holes such as would resemble a woven screen or a plate with a series of straight holes drilled through it. A "depth" filter resembles a piece of bread with a series of interconnecting passages. This "depth" filter is of a hydrophobic material which is commonly used in the medical field to prevent liquid passage while allowing air to pass. Examples of these air-liquid separator filters are described in the Reily U.S. Pat. No. 3,631,654, and Bujan U.S. Pat. No. 3,157,481.

I have unexpectedly found that by using relatively large pores of from 10 to 40 micron size in a "depth" filter of hydrophobic material, such as porous polytetrafluoroethylene marketed under the name Teflon (DuPont trademark), liquid can be filtered at very high filtering efficiencies for particles of 5 micron size and above. Normally liquid will not pass through such filter because of the liquid-shunning nature of the material. However, I have discovered liquid flow can be started through the filter by initiating a shock wave, such as a physical tap, to the filter after the filter has had one or more surfaces in contact with the parenteral solution for a period of 15 to 60 seconds. Once liquid starts through this hydrophobic filter an amazing thing happens. More than 90 percent of all particulate matter of 5 micron size and larger in the parenteral solution is filtered out by such hydrophobic filter.

This filtering occurs even though the passages are more than twice the size of the 5 micron size. I have found that in measuring and counting the filtered particles from a typical sterile parenteral solution that more than ½ of all particles filtered out fall in the 5–20 micron range, when filtering with a depth filter having a pore size of 20 to 30 micron size range. This hydrophobic filter of approximately ¼ inch diameter fits inside a rigid transparent housing where it is permanently secured by a special hydraulic assembly method and is connected directly to a venous needle.

This invention can be better understood with reference to the attached drawings.

THE DRAWINGS

DETAILED DESCRIPTION

Figure 1:
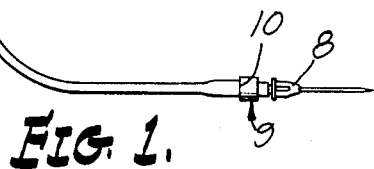
FIG. 1 is a front elevational view showing the filter device connected to an administration set at the venous needle.

Referring in detail to the attached drawings, FIG. 1 shows the system set up for administering parenteral solutions. The bottle 1 is suspended mouth downwardly from a hanger 2 above the patient. A tubular administration set has a spike 3 that is connected to an outlet of bottle 1. An air tube 4 in the bottle, permits air to enter the bottle as liquid is dispensed through the administration set. The administration set includes a spike 3, a drip housing 5, a flexible tube 6, a roller clamp 7 for controlling flow rates, and a venous needle 8. As shown in FIG. 1, a filter device generally indicated as 9 is connected between a distal end 10 of the flexible tube 6 and the venous needle 8. Thus, as liquid flows from bottle 1 through drip chamber 5 and conduit 6 it must pass through filter 9 before entering venous needle 8.

It is to this special "final" filter 9 at the venous needle that this invention relates. The special filter device is shown in an enlarged view in FIG. 2. This filter device includes a hollow housing 11 that has a forward adapter section 12 and a rearward adapter section 13. The forward adapter section 12 has a tapered needle adapter 14 and a protector adapter 15. A protruding rib 16 is used to indicate the direction of needle bevel of a hypodermic needle when attached to tapered adapter section 14. The rear adapter portion 13 includes a series of longitudinal ribs illustrated as 17 and 18. Over these ribs fit and end portion of flexible tube 6. If the filter device is sold preattached to tube 6 it can be permanently bonded to this tube. Otherwise if sold separately the adapter can be telescopically wedged into tube 6.

Figure 2:
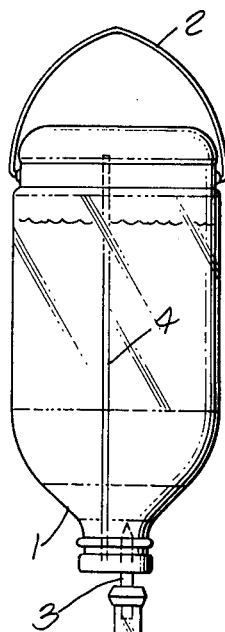
FIG. 2 is an enlarged side elevational view of the filter device disconnected from the venous needle and the administration set.
Figure 2:
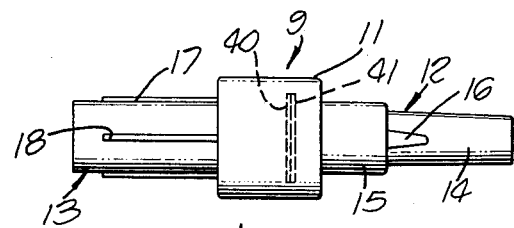
Figure 3:
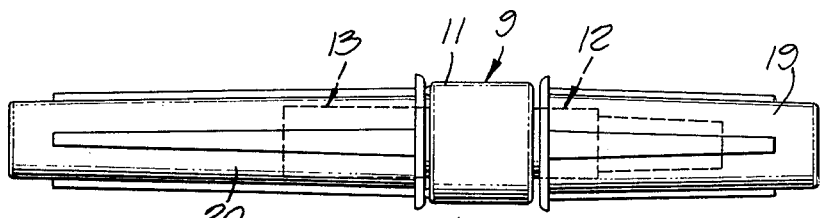
FIG. 3 is an enlarged side elevational view of the filter device showing removable protectors on opposite end portions of the device.

FIG. 3 shows the identical filter device of FIG. 2 with the hollow housing 11. However, here the forward adapter section 12 and the rearward adapter section 13 are covered respectively with removable protectors 19 and 20. If desired, these protectors can be reversed with the longer protector 20 on forward adapter section 12 and the shorter adapter 19 on rearward adapter section 13. Also, if desired the ribs 17 and 18 can be eliminated and a particular protector fitted to the rearward adapter 13 in an air tight fit. In this event a sterilizing vent can be made in through the protector on forward adapter 12.

Figure 4:
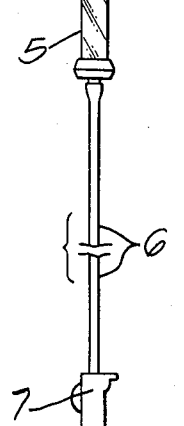
FIG. 4 is an enlarged exploded cross sectional view showing two parts of a hollow housing that contains the filter discs.
Figure 4:
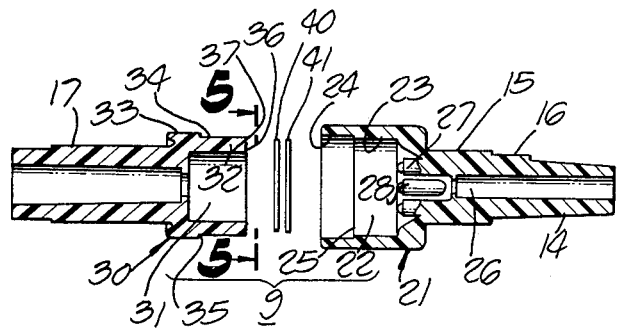

The internal structure of the filter device can best be seen in FIG. 4. Here there is a first hollow body member 21 that includes an enlarged chamber 22 that has an internal wall surface 23 and an internal wall surface 24. As noted in FIG. 4 the internal wall surface 24 is slightly larger than the wall surface 23 so as to provide a shoulder surface 25 therebetween. Directly adjacent an outlet passage 26 of the first body member 21 are a series of support prongs with rounded contact areas as illustrated at 27 and 28. The purpose of these prongs will be explained in more detail later.

Also forming a part of the housing is a second hollow body member 30. This hollow body member has a hollow chamber 31 defined by a skirt 32 that includes a rear outer wall surface 33 and a slightly smaller forward outer wall surface 34. There is shown in FIG. 4 a shoulder surface 35 between wall surface 33 and 34. At a forward end of the second hollow body member is an annular hydraulic pressure surface 36 forming a sharp annular wiper ring edge 37 at a juncture with forward outer wall surface 34. The importance of the wiper ring edge and hydraulic pressure surface will be explained in more detail with reference to FIG. 9.

Figure 5:
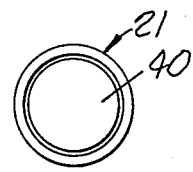
FIG. 5 is a sectional view taken along line 5—5 of FIG. 4.

In the exploded view of FIG. 4 are shown two hydrophobic depth filter discs 40 and 41. These two hydrophobic filter discs are firmly held in face-to-face relationship when the second hollow body member is telescopically urged into the chamber 22 of the first body member. In FIG. 5 the filter discs, with their circular shape, each have a thickness of 0.003 to 0.008 inch and a diameter of less than 0.375 inch. Preferably each disc has an effective area of 0.250 inch diameter. The discs are shown immediately before being pushed into the chamber 22 of the first hollow body member.

Figure 6:
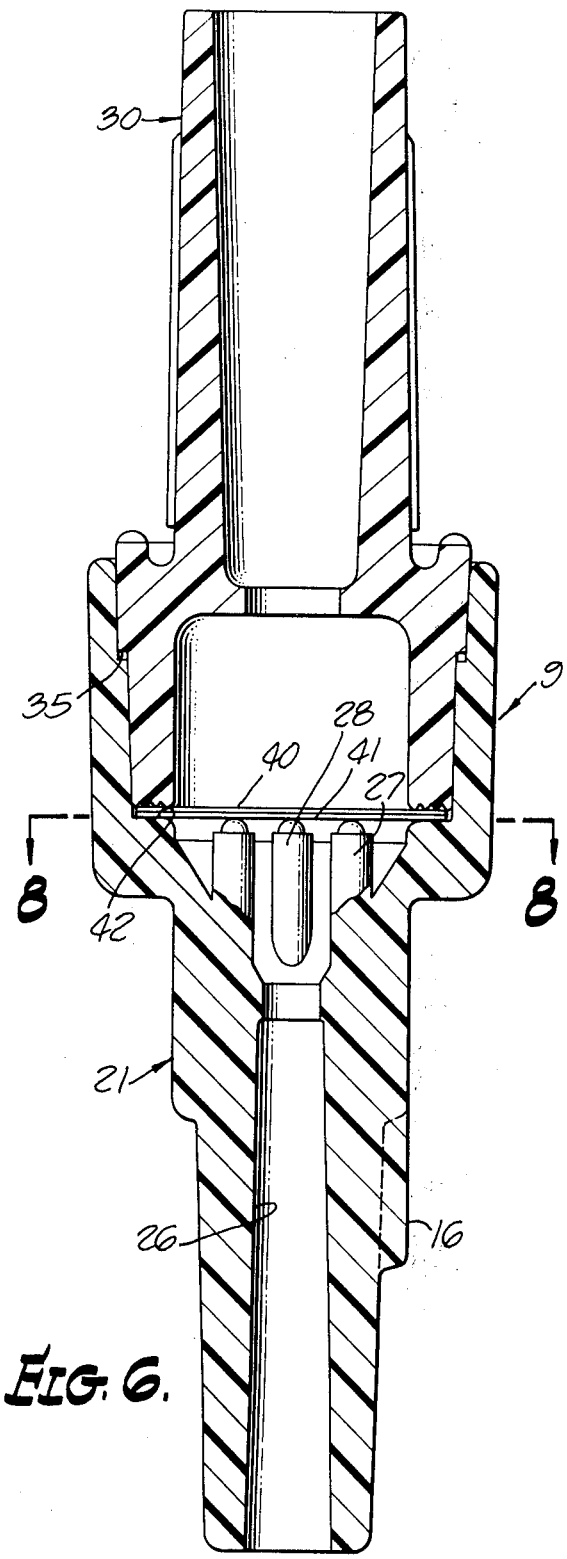
FIG. 6 is a further enlarged section view of the filter device shown in vertical position.

In FIG. 6 the special filter device is shown in a vertical position after the second body member 30 has been permanently assembled to the first body member 21. It is seen here that the two hydrophobic filter discs 40 and 41 are supported in a central area by support prongs illustrated as 27 and 28. The filter discs are also firmly urged against an annular sealing ledge 42.

Figure 7:
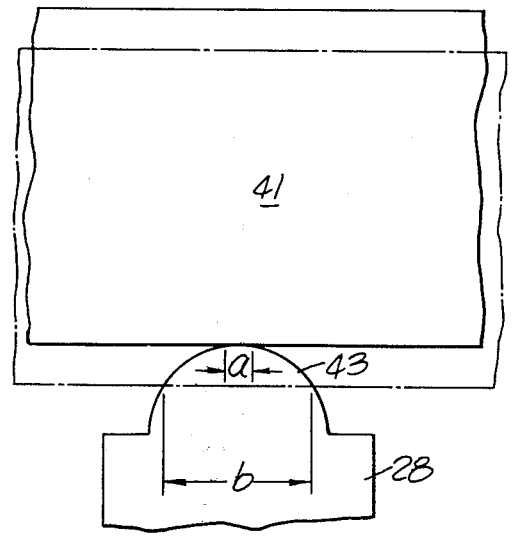
FIG. 7 is still a further enlarged view showing a rounded tipped support prong engaging one of the filter discs.

In FIG. 7 the support prong 28 is substantially enlarged. In this view it is clearly shown that the supporting surface is a rounded generally hemispherical-shaped crown surface 43. This support prong is on the downstream side of the hydrophobic filter discs. At very low liquid flow rates through the filter disc the disc rides up on the crowned support surface 43 so as to rest on a very small area which transverse dimension is illustrated generally as $a$. The purpose of this minimal contact with the filter is to maintain as much area as possible of the filter available for filtering so that the filter can be very small in size. A single prong 28 contacts less than 5 percent of the filter area under normal administration pressures. When four prongs are used they contact the filter over less than 20 percent of its area. In previous filters that used a checkerboard grid surface, sometimes as much as 50 percent of the effective filtering area was blocked out by the supporting grid structure. I have been able to provide a very small filter of approximately ¼ inch diameter in a highly efficient filtering device. Previous filter devices required filter discs as large as 1 to 2 inches in diameter. Such were extremely cumbersome for attaching to a venous needle.

The dotted lines in FIG. 7 illustrate the interrelationship between the filter disc and support prong 28 when a pressure surge of liquid comes through the filter device. Such might happen when a hypodermic syringe injects a medicament into the administration line under very high pressures. When this happens the filter disc 41 will sink down on support prong 28 and is temporarily supported by a broader crowned surface whose lateral dimension is indicated by the $b$. After the pressure surge has gone the filter disc 41 will again ride up high on the support prong 28 so that minimal filtering area of the filter disc is blocked off.

Figure 8:
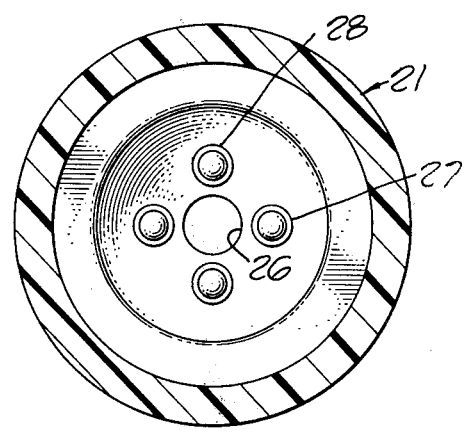
FIG. 8 is a sectional view taken along line 8—8 of FIG. 6.

FIG. 8 shows the top view of the support prongs of FIG. 6. Here is shown four support prongs, each having a hemispherical protruding crown portion of 0.035 to 0.060 inch diameter. I have found that this construction works very well and blocks out less than 20 percent of the effective filtering area of a filter disc of approximately ¼ inch in diameter.

Figure 9:
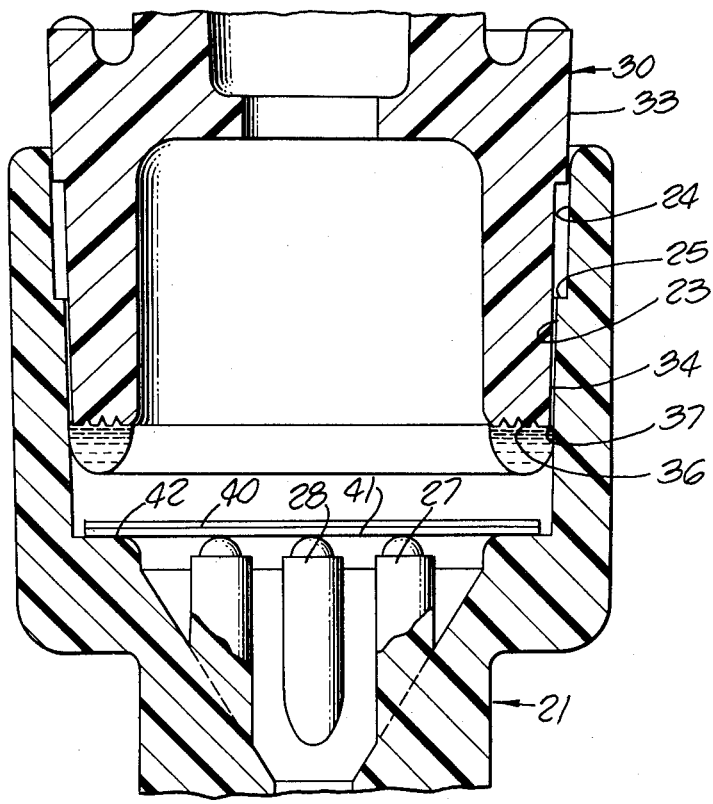
FIG. 9 is a further enlarged fragmentary sectional view showing the two parts of the housing being telescopically assembled together.

In the further enlarged fragmentary view of FIG. 9 a very important feature of the relationship of the filter housing and the filter discs is shown. In order for my special hydrophobic filter device to operate effectively as a final filter for parenteral solutions it is extremely important that the filter discs be permanently bonded about their peripheries to the filter housing. The importance of this cannot be overstressed because if there is any break in this peripheral seal to the housing, parenteral solution can flow around an edge of the filter disc and enter the venous needle in an unfiltered state. I have developed a very unique procedure for assembling the hollow body member 21 and second hollow body member 30 so that the disc is securely sealed to the housing.

As shown in FIG. 9 the first hollow body member has a sharp annular edge 37 and an annular hydraulic pressure surface 36. This pressure surface preferably has a series of annular grooves such as 38 and 39 with land surfaces therebetween. The grooves help pick up the solvent when the part is dipped in solvent and the lands help drive the solvent into the filter disc's pores. The sharp corner at 37 and hydraulic pressure surface 36 combine with outer wall surface 34 to create a piston effect. After the second body member 30 has been dipped in a solvent such as cyclohexanone the second body member is telescopically urged into the first body member 21. As this happens the cyclohexanone rolls along the hydraulic pressure surface 36 to create an annular rolling ring of solvent. I have discovered that substantially rounded surfaces corresponding to surface 36 and edge 37 and pressure surface 36 do not create an effective rolling ring of solvent. With the structure shown in FIG. 9 the rolling ring of solvent contacts the two hydrophobic filter members 40 and 41, and the hydraulic annular pressure surface drives this rolling ring of solvent and the solvent in the grooves through the pores of peripheral segments of both the hydrophobic filter disc 40 and filter disc 41 and firmly presses the discs against annular ledge 42.

As the two body members are pushed together the two filter discs become bonded, one to the first hollow body member 21 and one to the second hollow body member 30. The two body members are at the same time solvent bonded together. In this state the hydrophobic filter membranes take on a squeezed configuration at their peripheries such as shown at FIG. 6. I have found that this is an extremely reliable way to peripherally seal the two filters to the housing formed by the two hollow body members. Preferably, the hollow body members are of a transparent thermoplastic material. I have found that a rigid polypropionate works very well for the body members, but other materials could be used if desired.

Figure 10:
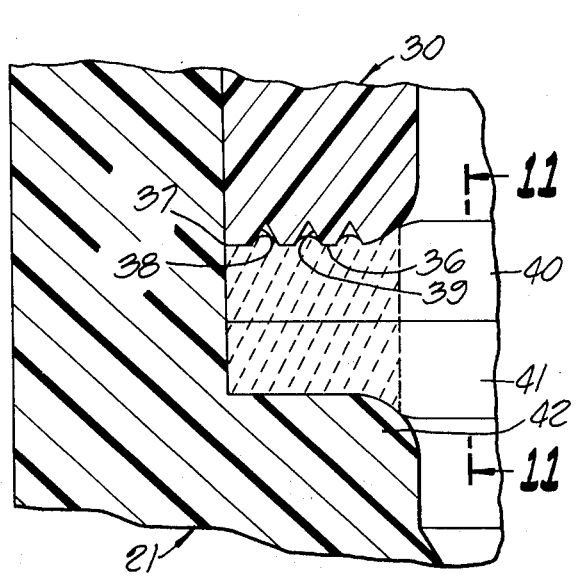
FIG. 10 is still a further enlarged fragmentary view showing the two filter discs permanently secured to the filter housing.

FIG. 10 is a still further enlarged fragmentary view showing just how the hydraulic force pushes the solvent into the pores of the filter member and permanently bonds it to the hollow body member. Such a sealing arrangement is very effective and does not rely on a particular degree of heating or welding.

Figure 11:
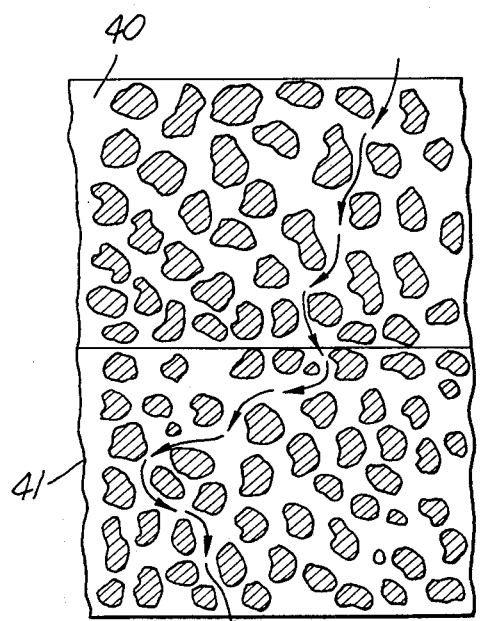
FIG. 11 is an enlarged schematic view showing an example of a random path liquid takes in its flow through the "depth" filter discs.

Once the filter device has been assembled the two filter discs 40 and 41 present a pair of "depth" filters in face-to-face relationship as shown in FIG. 11. A random path is shown by means of arrows to schematically illustrate a path liquid might travel through the hydrophobic filter discs. It is important to note that these two hydrophobic filter discs are of nonfibrous material so that no shedding of particles are likely to break off from the filter material.

Once the filter device has been assembled as described above and fitted to a parenteral solution administration set as shown in FIG. 1, the intravenous administration is ready to start. Because the filter discs are hydrophobic and of a nonwetting nature, there is a special procedure for starting the filtering through the discs. The parenteral solution flows down to the hydrophobic filter discs that have randomly interconnected stacked passages of from 10 to 40 micron size and preferably from 20 to 30 micron size. When the liquid first contacts this hydrophobic filter it will pass only very slowly, if at all, through its pores. The hydrophobic filter is of polytetrafluoroethylene. Polytetrafluoroethylene filters have been used before specifically to prevent liquid passage but allow air passage. Examples of this type for use for a hydrophobic filter are shown in U.S. Pat. Nos. 3,631,654 and 3,157,431 that describe an air purge system and an air inletting spike respectively. These previous hydrophobic filters were used to stop liquid passage through the filter.

I have discovered that with very large pore size of from 10 to 40 micron a hydrophobic filter will provide an amazing unit that will pass liquid. A shock wave, such as by a manual tap, sent through the filter device after the hydrophobic filter discs have "soaked" for 15 to 60 seconds, causes the liquid to freely flow through the hydrophobic filters that have interconnecting passages of from 10 to 40 micron. As liquid passes through these hydrophobic filters after the shock wave has initiated liquid flow provides an unexpected result. Even though the interconnecting passages are from 10 to 40 micron in size they filter out in excess of 95 percent of all particulate matter of 5 micron size and above if two discs as shown are used. In laboratory tests the filtering efficiency with the two discs of FIG. 6 averaged 97–98 percent removal of all particles of 5 micron size and above. Even with only one disc more than 90 percent of all particles of 5 micron size and above were removed.

This filtering action occurs with a very small type filter. By discovering this amazing effect I have developed a highly efficient final filter for parenteral solutions that need be only approximately ¼ inch in effective diameter or roughly the diameter size of the eraser on an end of a pencil. This is a tremendous advantage over previous final filters of the "wetting" or hydrophilic nature. These hydrophilic filters were often of from 1 to 2 inch diameter and their large housings were a burdensome weight on the venous needle sticking in the patient's arm.

With my invention I have provided a unique filter for parenteral solutions that is very small in size and is also very efficient. I have provided this by using an unexpected functioning of a hydrophobic filter of relatively large pore size. Such a filter does pass liquid after an initial shock wave and does filter out very small particulate matter.

Throughout the specification and the following claims I have used the word "hydrophobic" filter. By this term I mean to describe a filter of a generally non-wettable material, with polytetrafluoroethylene given as an example. The word "hydrophobic" has been used even though the filter does freely pass liquid after an initial shock wave has been sent through it.

In the foregoing specification and claims I have used a specific example to describe my invention. However, it is understood by those skilled in the art that certain modifications can be made to this embodiment without departing from the spirit and scope of the invention.

I claim:

1. A combination for filtering parenteral solution comprising: a parenteral solution bottle having means for suspending it above a patient, said bottle having a liquid outlet port; an administration conduit connected to said outlet port for draining parenteral solution from said bottle, said administration conduit having a dispensing end; a rigid thermoplastic transparent housing having a hollow chamber and a pair of tubular adapters communicating with this chamber and extending from opposite ends of the housing, one of said adapters being connected to the dispensing end of the administration conduit; a pair of disc-shaped filter membranes fitting inside the hollow housing and permanently secured in face-to-face relationship to the hollow housing, said filter membranes each being of less than 0.375 inch diameter and each having a thickness of from 0.003 to 0.008 inch and having a "depth" of randomly interconnected stacked passages of from 20 to 30 micron size, said membrane being of a nonfibrous hydrophobic material and presenting a porous hydrophobic structure impervious to at least 95 percent of all particulate matter of 5 micron size and greater from parenteral solution in the bottle passing through the filter's interconnected passages; said housing including a plurality of support prongs having rounded generally hemispherical end contact surfaces abutting a central portion of one of said filter membranes to support it during liquid flow therethrough, said support prongs covering less than 20 percent of the effective filter area of the filter membranes; and a hypodermic needle fitting over the other tubular adapter of the hollow housing.

2. A medical administration system that includes a container that has liquid therein and has an outlet connected to a depending tubular administration set for establishing a liquid head in the combined container and administration set for gravity dispensing liquid from a lower end of the administration set, wherein the improvement is: a hollow housing with an inlet and an outlet, said housing connected in series with the administration set below the container outlet, and a "depth" filter membrane of hydrophobic non-fibrous material with randomly interconnected stacked passages of from 10 to 40 micron size, said filter membrane fitting inside the housing and permanently sealed to the housing between its inlet and outlet at a sealed joint adjacent a periphery of the filter membrane, said filter membrane providing a porous hydrophobic structure impervious to at least 90% of all particulate matter of 5 micron size and greater from a parenteral liquid passing through its interconnected passages; and the housing has a plurality of support prongs having rounded generally hemispherical end contact surfaces engaging the filter membrane on its downstream side, said prongs blocking off less than 20% of the filter area bounded by the sealed joints, so that more than 80% of this filter area can pass liquid.

3. The combination as set forth in claim 2, wherein the hydrophobic filter membrane is of polytetrafluoroethylene.

4. The combination as set forth in claim 2 wherein the hydrophobic filter has interconnected passages of from 20 to 30 micron size.

5. The combination as set forth in claim 2, wherein the filter membrane is between 0.003 and 0.015 inch thick and has a diameter less than 0.375 inch, and the housing supporting this membrane is located adjacent a lower end of the administration set.

6. The combination as set forth in claim 2, wherein the filter membrane is comprised of a plurality of hydrophobic membrane layers of 0.003 to 0.008 inch thick, said membrane being impervious to 95 percent of all particulate matter of greater than 5 micron size.

7. The combination as set forth in claim 2, wherein the housing is formed of two hollow body members, a first body member telescopically fitting within a second body member and hermetically sealed together to seal the membrane within the housing, and the first hollow body member includes a hydraulic pressure surface and a wiper ring structure for hydraulically urging a bonding solvent through the passages of the filter membrane adjacent its periphery to permanently bond the membrane to the other hollow body member.

8. The combination as set forth in claim 7, wherein the hydraulic pressure surface includes a series of grooves for retaining a bonding solvent and a series of land surfaces for forcing solvent into passages of the membrane.

* * * * *